United States Patent
Sitzmann et al.

(10) Patent No.: US 9,872,802 B2
(45) Date of Patent: Jan. 23, 2018

(54) QUIET-OPENING WRAPPER

(75) Inventors: Stefan Sitzmann, Kirchehrenbach (DE); Michael Schuhmann, Grosshabersdorf (DE)

(73) Assignee: INFIANA GERMANY GMBH & CO. KG, Forchheim (DE)

( * ) Notice: Subject to any disclaimer, the term of this patent is extended or adjusted under 35 U.S.C. 154(b) by 471 days.

(21) Appl. No.: 14/000,936

(22) PCT Filed: Feb. 21, 2012

(86) PCT No.: PCT/EP2012/000748
§ 371 (c)(1),
(2), (4) Date: Oct. 7, 2013

(87) PCT Pub. No.: WO2012/113535
PCT Pub. Date: Aug. 30, 2012

(65) Prior Publication Data
US 2014/0014546 A1 Jan. 16, 2014

(30) Foreign Application Priority Data
Feb. 23, 2011 (DE) .................. 10 2011 012 209

(51) Int. Cl.
*C08L 23/06* (2006.01)
*A61F 13/551* (2006.01)
(Continued)

(52) U.S. Cl.
CPC .... *A61F 13/55135* (2013.01); *A61F 13/5514* (2013.01); *B32B 27/08* (2013.01);
(Continued)

(58) Field of Classification Search
CPC .......... A61G 13/5514; A61G 13/55135; A61G 13/5513; A61G 13/5516; A61G 13/55165;
(Continued)

(56) References Cited

U.S. PATENT DOCUMENTS 4,275,120 A 6/1981 Weiner
4,666,778 A 5/1987 Hwo
(Continued)

FOREIGN PATENT DOCUMENTS

DE 34 17 301 C2 12/1984
DE 691 02 267 T2 9/1994
(Continued)

OTHER PUBLICATIONS

English translation of the International Search Report dated Jul. 13, 2012.

*Primary Examiner* — Scott R Walshon
(74) *Attorney, Agent, or Firm* — Norris McLaughlin & Marcus, P.A.

(57) ABSTRACT

A wrapper that opens relatively quietly and wraps a sheetlike hygiene product provided on one side with an adhesive, said wrapper being based on a packaging material in web form and composed of a polymeric film comprising a) at least one heat-sealable layer based on a mixture of at least one $C_2$ or $C_3$ olefin homopolymer or copolymer and not more than 30% by weight, based on the total weight of the layer a), of polybutylene and b) optionally a layer of polyethylene having a density of 0.88-0.94 $g/cm^3$; the layer a), at least in those sections which face the regions of the hygiene product that are provided with the adhesive, has a release coating, and otherwise, at least in the sub-regions which are joined to form edge closures in the form of stripes or lines, has no release coating.

15 Claims, 2 Drawing Sheets

(51) Int. Cl.
*B32B 27/32* (2006.01)
*C09J 123/06* (2006.01)
*B32B 27/08* (2006.01)

(52) U.S. Cl.
CPC .............. *B32B 27/32* (2013.01); *C08L 23/06* (2013.01); *C09J 123/06* (2013.01); *B32B 2250/242* (2013.01); *B32B 2255/10* (2013.01); *B32B 2255/26* (2013.01); *B32B 2307/31* (2013.01); *B32B 2439/00* (2013.01); *B32B 2553/00* (2013.01); *C08L 2203/16* (2013.01)

(58) Field of Classification Search
CPC .......... A61G 13/5518; A61G 13/55175; A61G 13/551; B32B 27/08; B32B 27/32; C08L 23/06; C08L 23/08; C08L 23/087; C08L 23/0815; C08L 23/083; C08L 23/18; C08L 23/20; C08L 23/22
See application file for complete search history.

(56) References Cited

U.S. PATENT DOCUMENTS

| | | | |
|---|---|---|---|
| 4,882,229 A | 11/1989 | Hwo | |
| H1454 H * | 6/1995 | Cucuzza | A61F 13/5514 604/385.02 |
| 5,591,153 A * | 1/1997 | Mattingly, III | A61F 13/15747 604/385.05 |
| 5,591,498 A * | 1/1997 | Arakawa | A61F 13/60 428/343 |
| 5,972,473 A * | 10/1999 | Arakawa | A61F 13/551 28/152 |
| 6,500,160 B2 * | 12/2002 | Mizutani | A61F 13/551 206/440 |
| 6,716,203 B2 * | 4/2004 | Sorebo | A61F 13/551 604/385.02 |
| 9,271,879 B2 * | 3/2016 | Stone | A61F 13/15739 |
| 2001/0056270 A1 | 12/2001 | Mizutani et al. | |
| 2005/0131370 A1 * | 6/2005 | Hantke | A61F 13/551 604/385.02 |
| 2010/0233428 A1 * | 9/2010 | Stone | A61F 13/15739 428/133 |

FOREIGN PATENT DOCUMENTS

| | | |
|---|---|---|
| DE | 692 05 888 T2 | 5/1996 |
| DE | 199 09 839 B4 | 12/2004 |
| EP | 0 196 727 A1 | 8/1986 |
| EP | 0 435 789 A2 | 7/1991 |
| JP | 2006-223757 | 8/2006 |
| WO | 97/48554 A1 | 12/1997 |

* cited by examiner

QUIET-OPENING WRAPPER

This application is a 371 of International Patent Application No. PCT/EP2012/000748, filed Feb. 21, 2012, which claims foreign priority benefit under 35 U.S.C. §119 of the German Patent Application No. 10 2011 012 209.5, filed Feb. 23, 2011, the disclosures of which are incorporated herein by reference.

The invention relates to a wrapper with low noise opening for a sheet-like, single-side-adhesive hygiene product, which is based on a web of packaging material made of a plastics film which comprises a) at least one heat-sealable layer composed of a mixture of at least one $C_2$- or $C_3$-olefin-homo- or copolymer and at most 30% by weight, based on the total weight of the layer a), of polybutylene, and optionally conventional auxiliaries and b) optionally a layer of polyethylene with a density of from 0.88 to 0.94 $g/cm^3$, where the layer a) has a release coating at least in the sections which face toward the adhesive regions of the preferably folded hygiene product and which thus is bonded releasably, and has no release coating at least in the wrapper regions bonded to edge closures in the form of strips or lines.

It is known that for marketing sheet-like hygiene products in particular for women, each product is folded and individually packaged in packs with a varying number of items. For many users of these individually packaged hygiene products, the audible noise arising during opening of this type of individual packaging in order to remove the hygiene product is undesired and embarrassing, in particular when other people are likely to be present, e.g. in public toilets. Even if increased force is applied in order to open the package more rapidly and therefore to reduce the duration of the embarrassment, the conspicuous noise is still audible.

On the other hand, individual packages, such as wrappers of hygiene products, have consistently increased their importance, not only for reasons of hygiene but also because in most cases the products have immediate adhesion capability, permitting easy use. These single-side-adhesive sheet-like hygiene products, e.g. sanitary napkins, have been protected by wrappers that have increasingly been adapted to be appropriate to the adhesive hygiene product. Packages of this type are known to use packaging materials such as mono- or multilayer plastic films which have already been equipped on one side with a release coating, preferably indeed in accordance with the arrangement of the adhesive on the adhesive side of the hygiene product, and, alongside this, have no release coating, in particular no polysiloxane coating, at least in the regions of the plastics films that are necessary for the edge closures of the wrapper. This partial release coating of the film surface which faces toward the adhesive side of the hygiene product can also take the form of strips in the direction of the film webs, where no release coating is present at least in the sections of the film web from which the edge closures of the wrapper are produced via sealing or crimping or adhesion. It is thus possible, without any major technical cost, to use conventional heat-sealing processes or the more expensive crimping process to achieve good bonding of the wrappers at the lateral edges, without any need to use the needling process, which incurs very high maintenance costs and which has to be used for the bonding of packaging films that have also been siliconized in the edge-closure region.

Despite the production-technology advantages achieved through improvement of the packaging material, in particular through the arrangement of the release coating, in the individual packaging of single-side-adhesive hygiene products, no advantage has been obtained in relation to any prevention of the noise that arises during the opening of this type of package and that, as already mentioned, causes distress and embarrassment to the user.

It was therefore an object of the present invention to provide a wrapper with low noise opening for a single-side-adhesive hygiene product.

The invention solves said object by providing a wrapper with low noise opening for a sheet-like, preferably folded, single-side-adhesive hygiene product, which is based on a web of packaging material made of a mono- or multilayer plastics film which comprises a) at least one heat-sealable layer composed of a mixture of at least one $C_2$- or $C_3$-olefin-homo- or copolymer and at most 30% by weight, based on the total weight of the layer a), of polybutylene, and optionally conventional auxiliaries and b) optionally a layer of polyethylene with a density of from 0.88 to 0.94 $g/cm^3$, where the layer a) has a release coating at least in the sections which face toward the adhesive regions of the hygiene product and which thus is bonded releasably, and otherwise has no release coating, at least in the wrapper regions bonded to give edge closures in the form of strips or lines.

In the invention, the expression "low noise opening" means that evaluation of the noise arising during the opening of the package gives an energy equivalent permanent sound level $L_Aeq \leq 60$ dB. The definition of the energy equivalent permanent sound level $L_Aeq$ is based on measurement of the sound pressure level. The sound pressure level gives the intensity of a noise at a certain juncture, and generally exhibits variations over time. The amount of energy conveyed with the sound also varies with the sound pressure level. The energy equivalent permanent sound level is selected in such a way that if this were the constant sound pressure level it would convey the same quantity of energy. For the definition of noise limits the energy equivalent permanent sound level is preferred (cf. publication of the Austrian Environment Agency).

According to the present invention, the energy equivalent permanent sound level as defined before is reduced by at least 10% during the opening of the inventive wrapper for sheet-like single-side-adhesive hygiene products in comparison to wrappers already known or already available on the market for said products packaged therein, and the noise produced during the opening of the inventive package therefore corresponds to that of a low noise to normal conversation at 60 dB rather than to that of a loud conversation at about 70 dB (cf. publication of the Austrian Environment Agency at www.umweltbundesamt.at/umweltsituation/laerm/schalldruckpegel).

The packaging material used for the inventive wrapper with low noise opening is preferably a web of packaging material which is composed of a plastics film which can be a mono- or multilayer film.

To the extent that the plastics film is a monolayer film, it is composed of a heat-sealable layer composed of a mixture of a $C_2$- or $C_3$-olefin-homo- or copolymer and at most 30% by weight based on the total weight of the layer a), of polybutylene, and optionally conventional auxiliaries. It is preferable that the layer a) is composed of a mixture of a $C_2$- or $C_3$-olefin-homo- or copolymer and from 3 to 30% by weight, more preferably from 5 to 20% by weight, based on the total weight of the layer a), of polybutylene.

To the extent that the inventive packaging material is composed of a multilayer film, the composition of the sealable layer a) thereof corresponds to that of the monolayer film.

Materials suitable for producing the sealable layer a) of the mono- or multilayer film used as inventive packaging material are heat-sealable thermoplastic $C_2$- or $C_3$-olefin-homo- and/or copolymers. These suitable olefin-homo- and copolymers are preferably thermoplastic olefin-homo- or copolymers of ethylene and/or propylene optionally with other $\alpha,\beta$-unsaturated olefins having 6 to 10, i.e. 6, 7, 8, or 10 carbon atoms. Suitable olefin-homopolymers are polyethylenes (PE), preferably LDPE, or propylene-homopolymers (polypropylene, PP). "LDPE" means polyethylenes of low density which have a density in the range from 0.86 to 0.93 g/cm$^3$ and which feature a high degree of branching of the molecules. Suitable olefin-copolymers are preferably copolymers of ethylene and propylene, with a predominant portion of propylene, and copolymers of ethylene and of at least one $\alpha$-olefin having at least 6, preferably from 6 to 10, particularly preferably from 6 to 8 carbon atoms, very particularly preferably copolymers of ethylene or propylene with at least one $\alpha$-olefin selected from the group consisting of hexene and octene, the proportion of these in the olefin-copolymer preferably being at most 25 mol %, particularly preferably at most 15 mol %, based in each case on the total molecular weight of the olefin-copolymer. Suitable copolymers of ethylene and of at least one $\alpha$-olefin are LLDPE, VLDPE and m-PE. "LLDPE" means linear ethylene copolymers of low density which are characterized by the presence of a linear main chain with side chains located thereon and which have a density in the range from 0.86 to 0.94 g/cm$^3$. "mPE" means ethylene-copolymers which have been polymerized by means of metallocene catalysts and which preferably have a density in the range from 0.88 to 0.93 g/cm$^3$. "VLDPE" means linear ethylene copolymers of very low density, the density of these being in the range from 0.880 to 0.915 g/cm$^3$.

Materials particularly suitable as $C_2$- or $C_3$-olefin-homo- or copolymer component for producing the layer a) of the plastics film used are mixtures of LDPE and LLDPE, mixtures of LDPE and m-PE, mixtures of LDPE and VLDPE, and mixtures of ethylene-propylene-copolymers with a predominant proportion of propylene units and LLDPE and optionally LDPE, where the proportion of the ethylene-propylene-copolymer can be up to 50% by weight, based on the entire $C_2$- or $C_3$-olefin-homo- or copolymer component. It is very particularly preferable to use mixtures of LDPE and LLDPE which are composed predominantly of LDPE as mixture component for the polybutylene for producing layer a).

Conventional auxiliaries that can be added to the layer a) are color pigments and/or fillers, e.g. titanium dioxide or chalk, and the amount of these that can be present in the layer a) for matting and/or initial coloring purposes is preferably up to 20% by weight, based on the total weight of the layer a), with particular preference from 3 to 18% by weight, based on the total weight of the layer a).

To the extent that the packaging material used for producing the inventive wrapper is a multilayer film, said multilayer plastic film can have, adjacent to layer a), layer b) based on polyethylene with a density of from 0.88 to 0.94 g/cm$^3$. Materials that can preferably be used for producing layer b) are mixtures of LDPE and LLDPE which, like the layer a), can optionally comprise conventional auxiliaries, preferably those listed before. The mixtures of LDPE and LLDPE preferably comprise from 40 to 80% by weight of LDPE and from 60 to 20% by weight of LLDPE, in each case based on the total amount of the inventive mixture.

In another preferred embodiment of the present invention, the packaging material from which the inventive wrapper is produced comprises a multilayer film which has a layer b), which has on each of its surfaces a layer a).

Optionally, one surface of this type of multilayer film can also be bonded to a nonwoven web.

The inventive wrapper can also be composed of only a monolayer plastic film, i.e. of layer a), or of a two-layer plastics film made of one layer a) and one layer b), each of these films can be bonded to a nonwoven web.

This nonwoven web is preferably the external side of the inventive wrapper.

Preferably, the thickness of the layer a) is in the range from 3 to 10 µm and the thickness of the layer b) is in the range from 5 to 20 µm.

The mono- or multilayer plastics film used inventively as packaging material has a release coating on the layer a) at least in the sections which face toward the adhesive side of the packaged hygiene product and which therefore are releasably bonded, and has no release coating at least in the regions which, during the production of the wrapper, are bonded to give edge closures in the form of strips or to give linear edge closures.

Accordingly, the sections of the layer a) which are provided with a release coating are preferably arranged in the form of strips in the direction of the film web, and are preferably arranged in accordance with the arrangement of the adhesive sections of the hygiene product to be packaged.

It is preferable that the release coating is based on a polysiloxane which has been cured.

The inventive wrapper is produced by bringing at least the adhesive sections of the hygiene product to be packaged into contact with the release-coated sections of the plastics film used as packaging material. The two lateral sections of the portion of the plastic film, which is used as packaging material for the hygiene product, not covered by the hygiene product are optionally arranged together with the hygiene product, via folding these two lateral sections on the same surface of the hygiene product towards one another and optionally with overlap, in such a way that the edge strips of the packaging material section are mutually superposed. In order to bond these edge strips to one another in a way that is durable but permits opening, they are bonded via heat-sealing, adhesion, crimping or needling to give parallel lateral edge closures in the form of strips or in the form of single or multiple lines. Usually, the region which is associated with the optionally overlapping, folded lateral sections and which runs perpendicularly to the direction of the film web and, respectively, to the lateral edge closures, is not closed, in order to facilitate opening to remove the hygiene product.

BRIEF DESCRIPTION OF THE DRAWINGS

FIG. 1 describes a film web portion of an inventively used packaging material with a central release-coated longitudinal strip which for illustration is shown as somewhat longer than the adhesive hygiene product.

FIG. 2 is a wrapper 5 produced from the film web portion of the inventively used packaging material.

In FIG. 1, 1 indicates a portion of a multilayer plastics film web which is used as packaging material for producing an inventive wrapper 5. This portion has been provided with a release coating 2, and a sheet-like hygiene product 4 to be packaged in the wrapper 5 is placed on said portion. The hygiene product 4 is a sanitary napkin provided on its underside with a pressure-sensitive adhesive (not shown) which is bonded releasably on the release coating 2 and adheres without any loss of adhesion. In order to package the sanitary napkin, two lateral sections 1A and 1B of the portion 1, which have no release coating except in the region 2 are folded with said napkin along the fold lines C and D (shown as dotted line), and the mutually superposed edge strips 3, indicated by broken lines in FIG. 1, are bonded to one another in a manner that is durable but permits opening. These lateral parallel edge closures having the form of strips or of lines can be obtained via heat-sealing, adhesion, crimping or needling of the mutually superposed edge regions of the layer a). Preferably, the bonding of the edge regions to give edge closures in form of strips or of single or multiple lines is achieved via heat-sealing by means of known heat-sealing devices used for the sealing of packaging films.

FIG. 2 shows a finished wrapper 6, obtained via folding of the packaging sections 1A and 1B together with the sanitary napkin (hygiene product) 4 and sealing of the mutually superposed edge regions of the layer a) of the plastics film used as packaging material. The edge closure of the wrapper has already been partially opened in order to open the wrapper in region 3A, and has in region 3 still the form of a strip-like edge sealing of the inventive wrapper.

Figure 1:
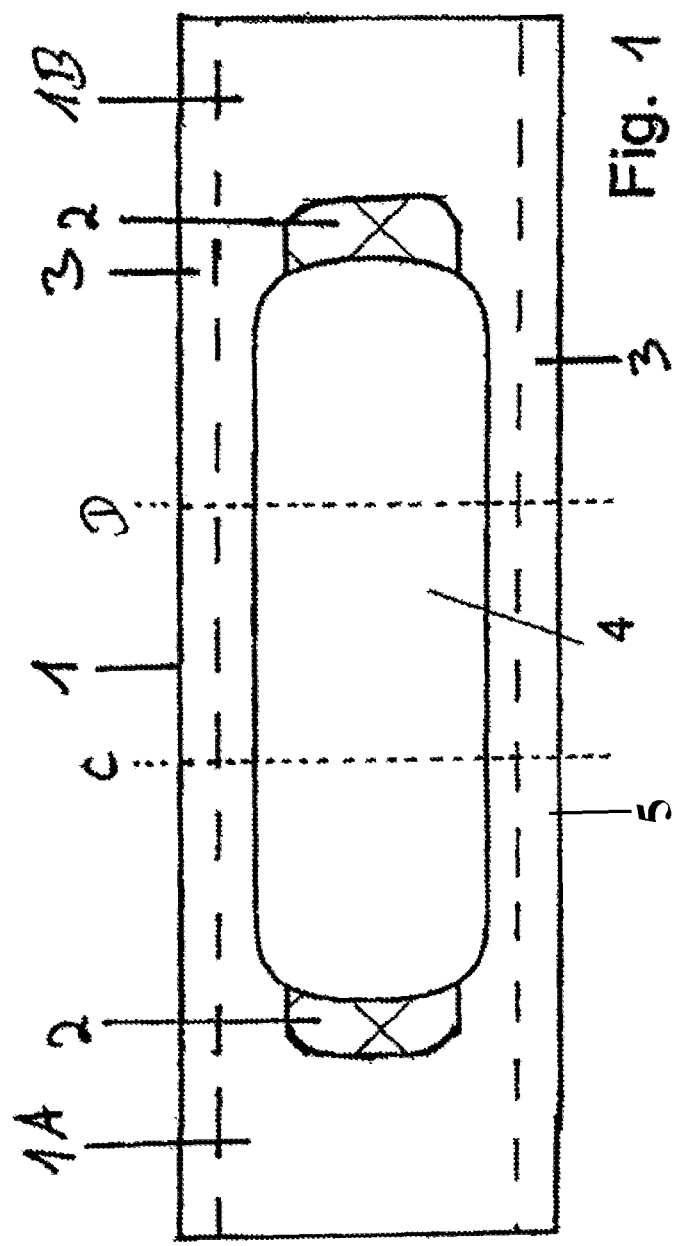
FIG. 1 shows an inventive wrapper before folding of the two lateral regions.
Figure 2:
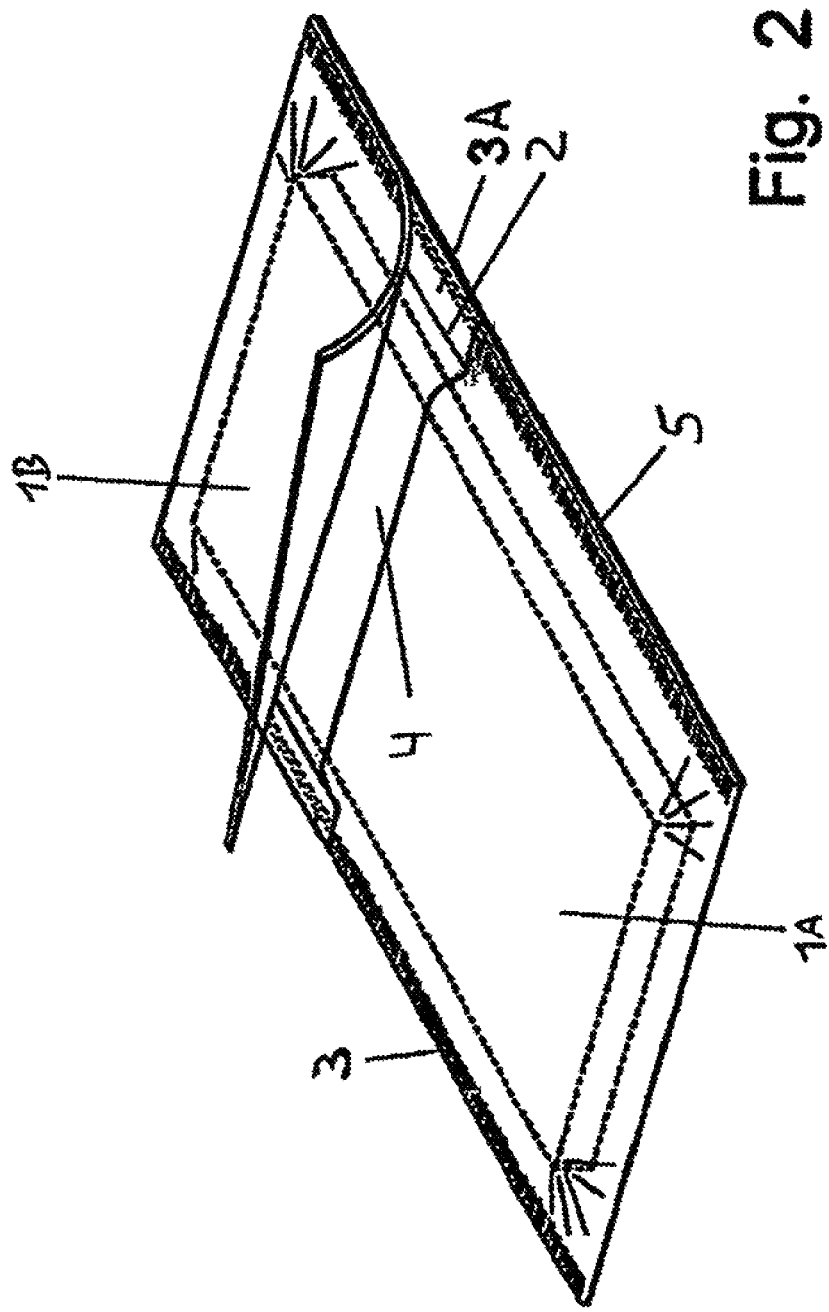
FIG. 2 is a diagram of the finished wrapper.

The inventive packages, preferably in the form of wrappers, are preferably suitable for providing single, individually packaged sheet-like hygiene products which are single-side adhesive, preferably by virtue of a pressure-sensitive adhesive. Preferably, said inventive package is an individual, single package for a sanitary napkin, for a panty liner or for a sheet-like incontinence product, which hygiene product is preferably packaged in folded form.

The present invention therefore further provides an individual, single package, preferably in the form of a wrapper of a sanitary napkin, a panty liner, or a sheet-like incontinence product, preferably in folded form packaged.

Key

| | |
|---|---|
| 1 | A portion of the inventive plastics film web as packaging material |
| 1A<br>1B | In each case a lateral section of the portion of the plastics film web |
| 2 | Release coating |
| 3 | Bonded edge strips/seal seam |
| 3A | Nonbonded section of edge strips 3 |
| 4 | Hygiene product |
| 5 | Wrapper |
| C<br>D | In each case a fold line of the hygiene product 4 to be packaged and of the portion of the packaging material |

Noise Measurement

I. Measurement conditions

Measurement equipment: 2250-L from Bruel & Kjaer

Software: BZ7133 Version 2.0.2

Space: Soundproof space, basal area 1 m×1 m and 2 m in height, equipped with walls to which sound-deadening nonwoven or woven fabric has been adhesive-bonded.

Distance between measurement equipment and 20 cm opening procedure

Opening rate: 3 cm/s

II. Description of Measurement Procedure

Each of 10 wrappers made of identical packaging film listed below, each with identical release coating and each with an identical folded sanitary napkin packaged therein, are opened at constant opening rate by the same person in a soundproof space (dimensions: W/L/H=1 m/1 m/2 m) at a distance of 20 cm from the measurement equipment.

$L_{Aeq}$ values are measured in the unit [dB]

The highest $L_{Aeq}$ measured in the unit [dB] during the opening of the sanitary napkin package is determined. $L_{Aeq}$[dB] is the equivalent continuous sound pressure level for an averaging time T. The averaging time T was defined as 1/10 seconds.

INVENTIVE EXAMPLES AND COMPARATIVE EXAMPLES

I. Polymers and Auxiliaries:

| | |
|---|---|
| LDPE (polyethylene of low density) | Lupolen 2420 F from Basell |
| Chalk masterbatch (72% by weight chalk in LDPE) | Multibatch ME 50009 from Multibase |
| Polybutylene | Polybutene 8640 M from Basell |
| LLDPE (linear polyethylene of low density) | Innovex LL 6910 from BP |
| Color masterbatch (70% by weight of $TiO_2$ in LDPE) | Remafin Weiss RCL from Clariant |

II. Production of the Wrapper

The films listed as packaging material in the table below, each having a release coating made of cured polysiloxane in the respective adhesive region of the sanitary napkin to be packaged, were used as described above to produce wrappers of which the edge closures, 0.5 mm in width, were produced via sealing of the mutually superposed foil sections of the layer a) with the aid of a sealing tool with heatable sealing jaws with an applied pressure of 4.5 bar at a temperature of 105° C. and a sealing time of 0.5 sec. The % data are always % by weight.

III. Film Structure

| | Film structure of packaging material | Edge closures of package (0.5 mm) |
|---|---|---|
| Comparative examples | | |
| Comparative example 1 | LDPE<br>(Monolayer film, thickness 25 μm) | sealed |
| Comparative example 2 | 56% of LDPE + 22.5% of chalk masterbatch + 19.5% of LLDPE + 2% of color masterbatch<br>(Monolayer film, thickness 25 μm) | sealed |

|  | Film structure of packaging material | Edge closures of package (0.5 mm) |
|---|---|---|
| Inventive examples | | |
| Inventive example 1 | 85% of LDPE + 15% of polybutylene (Monofilm, thickness 25 μm) | sealed |
| Inventive example 2 | 39% of LDPE + 19% of chalk masterbatch + 25% of LLDPE + 2% of color masterbatch + 15% of polybutylene (Monolayer film, thickness 25 μm) | sealed |
| Inventive example 3 | Layer a [thickness: 5 μm]: 39% of LDPE + 19% of chalk masterbatch + 25% of LLDPE + 2% of color masterbatch + 15% of polybutylene Layer b [thickness: 15 μm]: 56% of LDPE + 22.5% of chalk masterbatch + 19.5% of LLDPE + 2% of color masterbatch Layer a [thickness: 5 μm]: 39% of LDPE + 19% of chalk masterbatch + 25% of LLDPE + 2% of color masterbatch + 15% of polybutylene (3-layer film) | sealed |

IV. Noise Measurement Results During Opening

| Measurement | $L_{Aeq}$[dB] Comparative example 1 | $L_{Aeq}$[dB] Comparative example 2 | $L_{Aeq}$[dB] Inventive example 1 | $L_{Aeq}$[dB] Inventive example 2 | $L_{Aeq}$[dB] Inventive example 3 |
|---|---|---|---|---|---|
| 1 | >70 | >70 | 59.9 | 59.8 | 60 |
| 2 | >70 | >70 | 60.1 | 59.7 | 59.1 |
| 3 | >70 | >70 | 58.3 | 57.9 | 58.5 |
| 4 | >70 | >70 | 60.2 | 59 | 58.7 |
| 5 | >70 | >70 | 59.4 | 60.1 | 59.5 |
| 6 | >70 | >70 | 58.7 | 58.2 | 58.1 |
| 7 | >70 | >70 | 59.9 | 59.1 | 58.2 |
| 8 | >70 | >70 | 58.2 | 57.7 | 58 |
| 9 | >70 | >70 | 60 | 58.2 | 57.6 |
| 10 | >70 | >70 | 58.9 | 58.7 | 58.4 |
| Average value: [dB] | >70 | >70 | 59.36 | 58.84 | 58.61 |

The noise measurements were made in accordance with the methods stated before.

Results:

The noise measurements show that the inventive packages can be opened with less noise than packages of packaging material having no inventive layer a). Furthermore each of the packages according to the comparative examples can be opened only with irreversible damages to the packaging material.

What is claimed is:

1. A wrapper with a low noise opening giving an energy equivalent permanent sound level $L_{Aeq} \leq 60$ dB for a sheet-like, single-side-adhesive hygienic product, which wrapper is formed of packaging material in web form and comprises a plastic film comprising:
   a) at least one heat-sealable layer comprising a mixture of at least one homopolymer of ethylene or propylene or of at least one olefin-copolymer selected from the group consisting of copolymers of ethylene and propylene with a predominant portion of propylene units and of copolymers of ethylene and of at least one α-olefin having 6 to 10 carbon atoms, and from 5 to 20% by weight, based on the total weight of the layer a), of polybutylene, and optionally conventional auxiliaries and
   b) optionally a layer of polyethylene with a density of from 0.88 to 0.94 g/cm$^3$, where the layer a) has a release coating in sections which face toward adhesive regions of the hygienic product and which thus is bonded releasably thereto, and otherwise has no release coating in wrapper regions bonded as edge closures in the form of strips or lines.

2. The wrapper as claimed in claim 1, wherein the plastic film comprises at least one layer b) which has at least on one surface a layer a).

3. The wrapper as claimed in claim 1, wherein the at least one layer a) or the film of at least one layer a) and b) is bonded to a nonwoven web as backing layer adjacent to a layer a) or to a layer b).

4. The wrapper as claimed in claim 1, wherein the polyethylene component of the layer b) comprises a mixture of low density polyethylene (LDPE) and linear low density polyethylene (LLDPE).

5. The wrapper as claimed in claim 1, wherein said at least one homopolymer of ethylene or propylene or said at least one olefin-copolymer in the at least one layer a) is a polyethylene (PE), a polypropylene, a mixture of LDPE and LLDPE, a mixture of LDPE and metallocene-catalyzed polyethylene (m-PE), a mixture of LDPE and very low density polyethylene (VLDPE), or a mixture of an ethylene-propylene-copolymer having a predominant proportion of propylene units and of LLDPE and optionally LDPE.

6. The wrapper as claimed in claim 1, wherein the at least one layer a) comprises color pigments and/or fillers as conventional auxiliaries.

7. The wrapper as claimed in claim 1, wherein the release coating is based on a cured polysiloxane coating.

8. The wrapper as claimed in claim 1, wherein the sections with the release coating on the at least one layer a) are arranged in the form of strips and/or correspond to an arrangement of the adhesive regions of the packaged hygienic product.

9. The wrapper as claimed in claim 1, wherein each of the edge closures of the wrapper in form of strips or of single or multiple lines, are durable bonds of the sections without any release coating on the at least one layer a), obtained by superposing the edges of these regions by folding two lateral sections of the packaging material toward one another and together with the hygienic product to be packaged and optionally with overlap on the same surface of the hygiene product during the packaging.

10. The wrapper as claimed in claim 9, wherein the durable bonds are obtained via heat-sealing, adhesion, crimping, or needling.

11. The wrapper as claimed in claim 1, wherein the wrapper is used for individual packaging of a single hygienic product.

12. The wrapper as claimed in claim 11, wherein the single packaged hygienic product is a sanitary napkin, a panty liner or a sheet-like incontinence product.

13. The wrapper as claimed in claim 1, wherein the plastic film is a matt, optionally colored, plastic film.

14. The wrapper as claimed in claim 1, wherein the wrapper is based on the plastic film.

15. A combination comprising (A) a sanitary napkin, panty liner, or sheet-like incontinence product packaged within (B) the wrapper as claimed in claim 1.

* * * * *